United States Patent
Smith (10) Patent No.: US 10,960,454 B2
(45) Date of Patent: Mar. 30, 2021

(54) ACETABULAR PROSTHESIS

(71) Applicant: Biomet Manufacturing, LLC, Warsaw, IN (US)

(72) Inventor: Aaron P. Smith, Warsaw, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 861 days.

(21) Appl. No.: 13/746,033

(22) Filed: Jan. 21, 2013

(65) Prior Publication Data

US 2013/0199259 A1    Aug. 8, 2013

Related U.S. Application Data

(60) Provisional application No. 61/595,911, filed on Feb. 7, 2012.

(51) Int. Cl.
| | | |
|---|---|---|
| B21D 53/00 | (2006.01) | |
| B21D 37/20 | (2006.01) | |
| A61F 2/30  | (2006.01) | |
| A61F 2/34  | (2006.01) | |

(52) U.S. Cl.
CPC .......... *B21D 53/00* (2013.01); *A61F 2/30942* (2013.01); *A61F 2/34* (2013.01); *B21D 37/20* (2013.01); *A61F 2002/30578* (2013.01); *A61F 2002/30948* (2013.01); *A61F 2002/30957* (2013.01)

(58) Field of Classification Search
None
See application file for complete search history.

(56) References Cited

U.S. PATENT DOCUMENTS

| | | |
|---|---|---|
| 6,162,257 A  | 12/2000 | Gustilo et al. |
| 6,327,491 B1 | 12/2001 | Franklin et al. |
| 6,944,518 B2 | 9/2005  | Roose |
| 6,978,188 B1 | 12/2005 | Christensen |
| 7,162,322 B2 | 1/2007  | Arbogast et al. |
| 7,713,306 B2 | 5/2010  | Gibbs |

(Continued)

FOREIGN PATENT DOCUMENTS

WO    WO-2010129660 A1    11/2010

OTHER PUBLICATIONS

MAX-Ti™ Modular Protrusio Cage Surgical Technique, Biomet Orthopedics, Inc., 10 pages (2003).

(Continued)

*Primary Examiner* — Mohammad Ali
*Assistant Examiner* — Saad M Kabir
(74) *Attorney, Agent, or Firm* — Schwegman Lundberg & Woessner, P.A.

(57) ABSTRACT

A method of making a custom acetabular implant for a patient. The method comprises acquiring and analyzing tomography data of the patient, and obtaining geometry and measurement parameters of the patient's pelvic anatomy. A standard acetabular prosthesis blank is selected from a plurality of pre-manufactured blanks, and includes a cup portion and at least one flange. The method includes shaping the blank acetabular prosthesis using a custom deforming fixture such that the shaped acetabular prosthesis has a final shaped geometry and measurement parameters to substantially match the patient's pelvic anatomy relative to the patient's acetabulum.

17 Claims, 7 Drawing Sheets

(56) References Cited

U.S. PATENT DOCUMENTS

| | | |
|---|---|---|
| 2007/0106389 A1 | 5/2007 | Croxton et al. |
| 2007/0118243 A1 | 5/2007 | Schroeder et al. |
| 2010/0286789 A1 | 11/2010 | Meridew |
| 2010/0292963 A1* | 11/2010 | Schroeder .................. A61F 2/30 703/1 |
| 2011/0029091 A1 | 2/2011 | Bojarski et al. |
| 2011/0295378 A1* | 12/2011 | Bojarski ............. A61F 2/30942 623/20.35 |

OTHER PUBLICATIONS

PAR 5™ Protrusio Acetabular Reconstruction System, Biomet Orthopedics, Inc., 12 pages (2006).

* cited by examiner

ACETABULAR PROSTHESIS

CROSS-REFERENCE TO RELATED APPLICATIONS

This application claims the benefit of U.S. Provisional Application No. 61/595,911, filed on Feb. 7, 2012. The entire disclosure of the above application is incorporated herein by reference.

INTRODUCTION

The present technology relates to hip medical implants, and methods of their manufacture.

A natural hip joint may undergo degenerative changes due to a variety of etiologies. If these degenerative changes become so far advanced and irreversible, it may ultimately become necessary to replace a natural hip joint with a prosthetic hip. When implantation of such a hip joint prosthesis becomes necessary, the head of the femur, the acetabulum, or both may need to be replaced. If the acetabulum needs repair, all remnants of articular cartilage are generally removed from the acetabulum. An acetabular prosthesis that will accommodate the head or ball of the hip prosthesis may be affixed to the acetabulum by means of cement, screws or other appropriate fixation means.

Due to any number of reasons, however, a small portion of patients that undergo such orthopedic surgical procedures may require subsequent revision surgery to replace the prosthetic device with a new prosthetic device generally referred to as a revision prosthesis.

In this regard, a revision acetabular prosthesis may generally include additional mounting points, such as flange members or hooks that provide additional stability for the revision acetabular prosthesis. These additional mounting points are generally needed due to additional bone loss or defects exhibited at the acetabulum, such as collar/rim defects or pelvic discontinuity defects.

Various types of revision acetabular prostheses are currently available and different surgeons prefer different types of revision acetabular prostheses. Some surgeons prefer to use what are known as ilium, pubis, and/or ischium flanges that are used with the acetabular prosthesis and enable further securement of the acetabular prosthesis in the ilium, pubis, and/or ischium regions of the pelvis. During surgical procedures, the ilium, pubis, and/or ischium flanges may be shaped to match and mate with the patient's pelvis anatomy. This may lead to increased surgical times, cost, and complexity. Because of this, a hospital may maintain a large inventory of different revision acetabular cups to meet the various surgeons' preferences. Still further, the surgeon generally may require trials or several revision acetabular cups to be available during surgery to account for any type of condition that may arise during the surgical procedure. This increased inventory of prosthetic devices increases the overall hospital costs and inventory control. Accordingly, there remains a continued need to provide less costly and time saving custom-made orthopedic implants having enhanced strength.

SUMMARY

The present disclosure generally provides a method of making a custom acetabular implant for a patient. The method comprises analyzing tomography data of the patient and obtaining geometry and measurement parameters of the patient's pelvic anatomy. An acetabular prosthesis blank is then selected from a plurality of pre-manufactured acetabular prosthesis blanks, each acetabular prosthesis blank including a cup portion and at least one flange. The method includes shaping the acetabular prosthesis blank using a custom deforming fixture to form a custom acetabular prosthesis, wherein the custom acetabular prosthesis has a final shaped geometry and measurement parameters that substantially match the patient's pelvic anatomy relative to the patient's acetabulum.

In another embodiment, the method begins with acquiring various tomography data of the patient. The tomography data is then analyzed and geometry and measurement parameters of the patient's pelvic anatomy are obtained. A custom deforming fixture is obtained having dimensions modeled after the tomography data and to match the geometry and measurement parameters relative to the patient's acetabulum. An acetabular prosthesis blank is selected from a plurality of pre-manufactured acetabular prosthesis blanks that include a cup portion with at least one integral flange radially extending therefrom. The selected blank has measurement parameters substantially similar to the patient's pelvic anatomy. The method includes customizing and shaping the acetabular prosthesis blank using the deforming fixture to shape the flange such that the shaped acetabular prosthesis will substantially mate with the patient's pelvic anatomy relative to the patient's acetabulum.

In yet another embodiment, the method includes acquiring tomography data of the patient and analyzing the tomography data to obtain geometry and measurement parameters of the patient's pelvic anatomy. A patient-specific configuration of the patient's pelvic anatomy relative to the patient's acetabulum is then determined. The method includes obtaining a custom press die mold having dimensions substantially matching the patient-specific configuration. The press die mold may be a two piece mold. An acetabular prosthesis blank is selected from a plurality of pre-manufactured monolithic acetabular prosthesis blanks that include a cup portion and a plurality of integrally formed flanges radially extending therefrom. The selected blank has measurement parameters substantially similar to the patient's pelvic anatomy. The acetabular prosthesis blank is then deformed using the custom press die mold and at least one of the plurality of flanges is shaped to achieve the patient-specific configuration.

It should be noted that the figures set forth herein are intended to exemplify the general characteristics of materials, methods and devices among those of the present technology, for the purpose of the description of certain embodiments. These figures may not precisely reflect the characteristics of any given embodiment, and are not necessarily intended to define or limit specific embodiments within the scope of this technology.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

The present technology relates to hip arthroplasty implant components and methods for improving the strength and usefulness of medical implants. The medical implant can be an orthopedic implant, for example, a hip revision, a total hip assembly or replacement, and the like. The medical implant can also be custom made or a generic shape that can be deformed for filling in a bone defect caused by surgical intervention or disease. As used herein, the term "implant" may be used to refer to an entire implant, or a portion thereof; portions may be as large or as small as necessary to accommodate the specific need. For example, an implant made in accordance with the present disclosure, generally including an acetabular cup, or dome, with at least one integral flange extending therefrom, may constitute the entire implant, or it may be used with one or more pieces or components that together form a final implant or implant assembly. As such, the present disclosure encompasses a wide variety of therapeutic and cosmetic applications, in human or other animal subjects, and the specific materials and devices used must be biomedically acceptable. As used herein, such a "biomedically acceptable" component is one that is suitable for use with humans and/or animals without undue adverse side effects (such as toxicity, irritation, and allergic response) commensurate with a reasonable benefit risk/ratio.

Generally, the present disclosure provides methods and tools to produce implantable acetabular prostheses that are custom deformed and will substantially precisely fit individual patients with substantially no gain or loss of material, and without the need for additional components such as spacers or the like. Revision hip patients often present challenging defects that may not be fully addressed with thin prostheses that, while allowing easy bending and manipulation, sacrifice strength or durability. In this regard, the present disclosure provides for the creation of a strong, custom shaped acetabular prosthesis that substantially matches the patient's unique anatomy without having to modify or alter the shape of the prosthesis during the actual surgical procedure. Further, the present disclosure generally provides that each custom shaped acetabular prosthesis is modified from a select set of pre-manufactured blanks of a limited number of sizes, such as about a dozen or so size variations, eliminating the costly need to make a custom implant from scratch, or to maintain a large inventory of acetabular prostheses each with various differences in shape to accommodate the practically infinite variations of patient needs.

Figure 1:
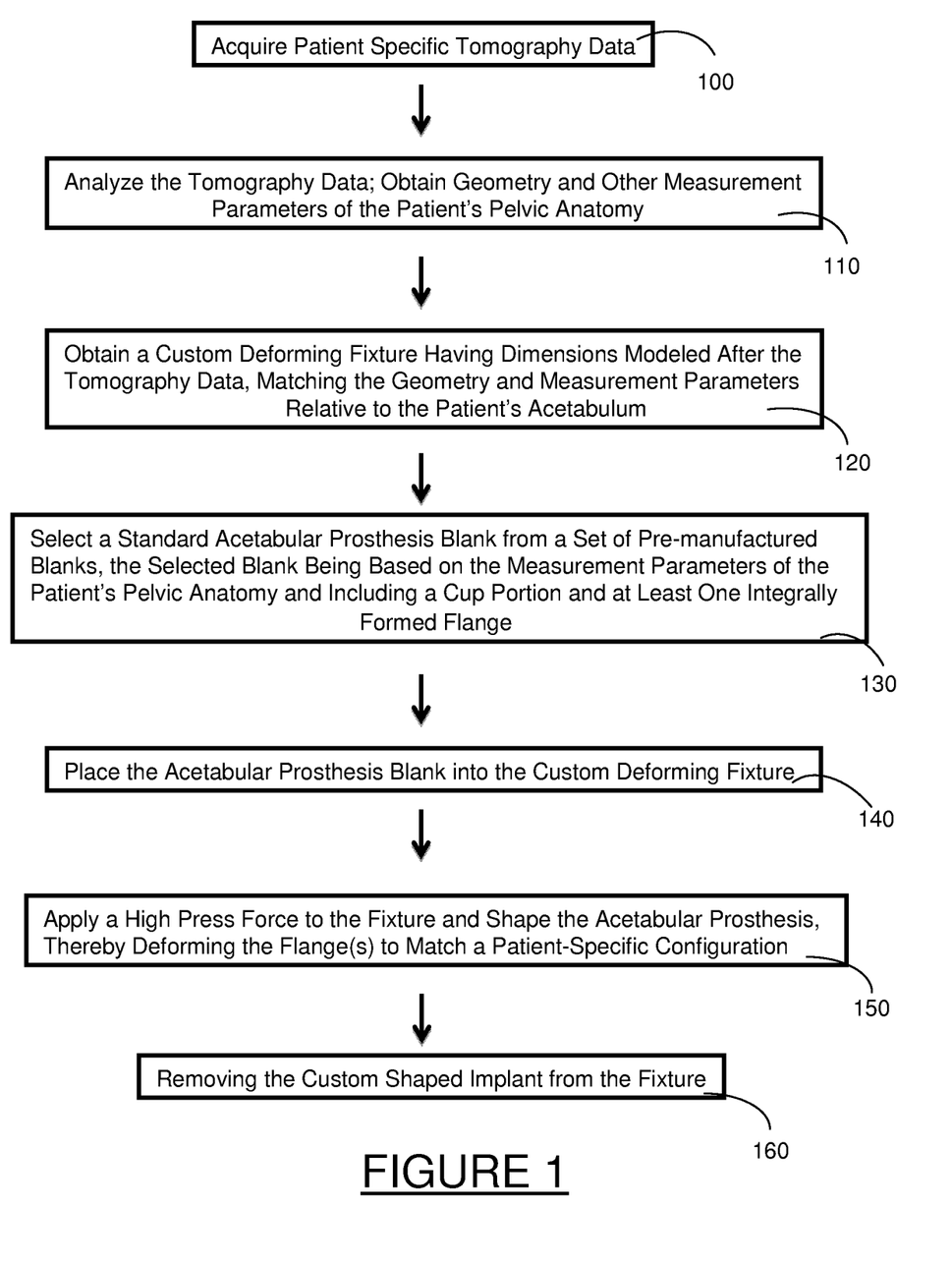
FIG. 1 is a flow chart of an exemplary method of making a custom shaped acetabular prosthesis, in accordance with various aspects of the present disclosure.
Figure 2A:
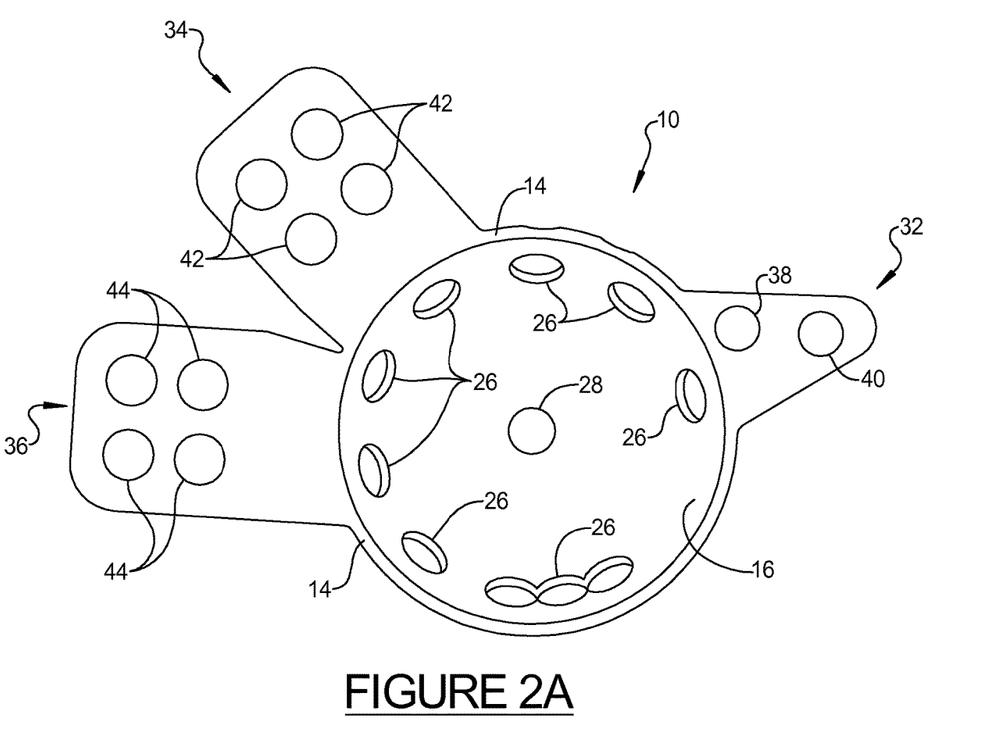
FIG. 2A a front plan view of an acetabular prosthesis blank, in accordance with various aspects of the present disclosure.
Figure 2B:
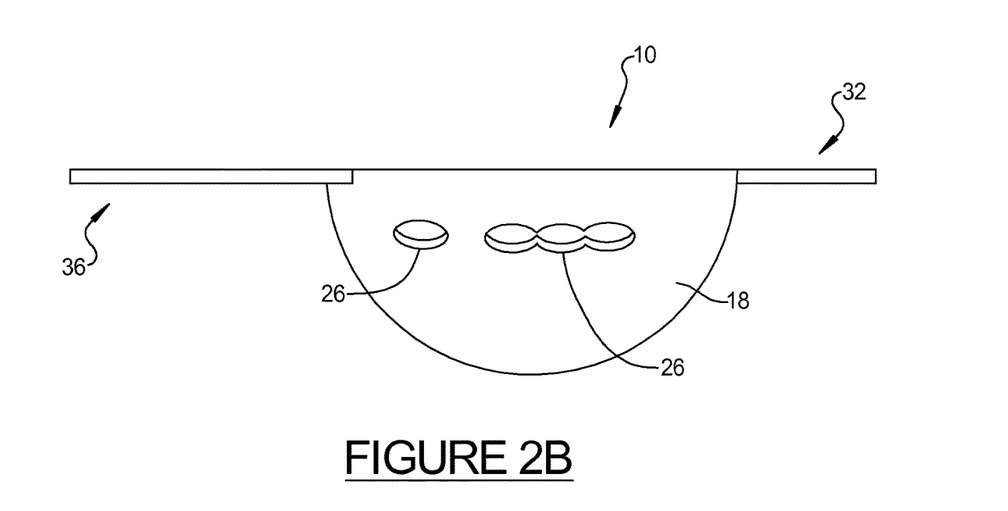
FIG. 2B is a side plan view of the acetabular prosthesis blank shown in FIG. 2A.
Figure 2C:
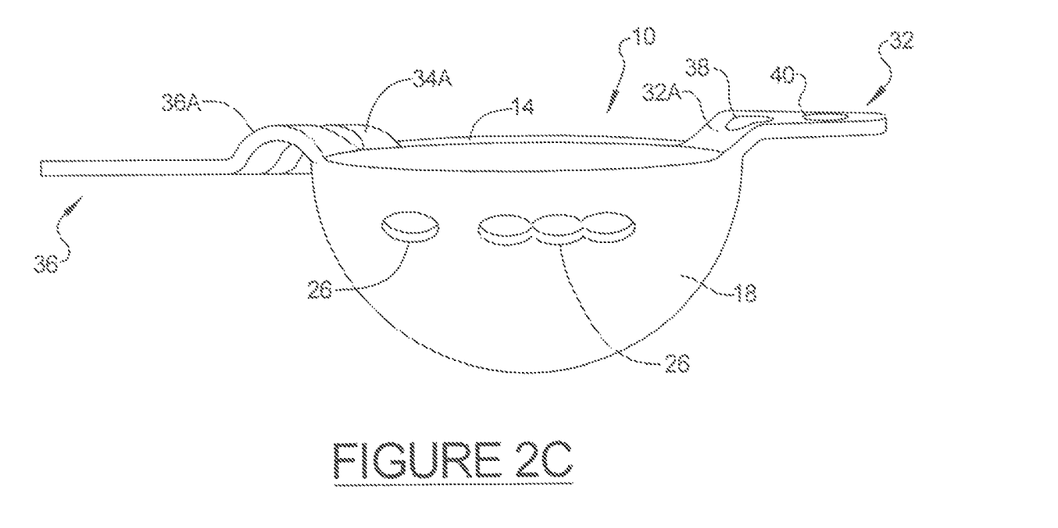
FIG. 2C is a side plan view of another acetabular prosthesis blank in accordance with various aspects of the present disclosure.

FIG. 1 provides a flow chart of an exemplary method of making a custom shaped acetabular prosthesis in accordance with the present disclosure. As shown in step 100, tomography data is obtained for a specific patient. As used herein, "tomography data" may include various imaging data that is received from known scanning techniques, such as ultrasound, laser interferometry, magnetic resonance imaging (MRI), X-Ray, computed tomography (CT), positron emission tomography (PET), and the like. With reference to step 110, once the data is obtained, it is analyzed to obtain various geometry and other measurement parameters (i.e., distances between structural or bony landmarks, the location of gaps, angles, key tissues and ligaments, other interferences, etc.) of the patient's pelvic anatomy, and in particular, parameters that are relative to the patient's acetabulum, including any damaged areas or areas that may need restructuring. Such analysis may include both two and three dimensional modeling.

In order to fully analyze the data, in various aspects, the data may be used with computer aided design (CAD) software as is known in the art. In this regard, one or more three-dimensional representations of the patient's pelvic anatomy can be created. For example, the data can be used to create three-dimensional solid models that can be used with computer aided engineering analyses as are known in the art, including finite element analysis, behavior modeling, and various functional component simulations. Such models can be used for modeling biological tissue and bone structure, and according to the present disclosure, used to assist the manufacture of a custom deforming device, or press die mold, as discussed below. In various aspects, this may include the creation of a digital representation of the patient's complete hip and pelvis region, or simply a portion thereof. In many instances, it may be useful to particularly obtain geometry and measurement parameters relative to at least one of the ischium, pubic, and/or ilium bone structures of the patient.

Collection and analysis of the above data, geometry, and measurement parameters allows one to accurately determine a patient-specific configuration of the patient's pelvic anatomy, and with particular regard to the patient's acetabulum.

With reference to step 120, a custom deforming fixture is obtained or manufactured having dimensions modeled after the tomography data. In this regard, the custom deforming fixture preferably substantially matches the patient-specific configuration in a very precise manner, and accounts for most, if not all, of the relevant geometry and other measurement parameters of the patient's pelvic anatomy relative to the acetabulum and/or nearby area requiring repair or attention. The custom deforming fixture is manufactured using methods known in the art. In various aspects, the actual patient-specific tomography data (raw or processed) and/or the three-dimensional solid models are used to create a fixture or mold that accurately reflects the bone and tissue structure of the patient. The custom deforming fixture may comprise steel, or other metal or alloy of sufficient strength to mold, shape, and/or deform the acetabular prosthesis. In many embodiments, the deforming fixture may be a two-piece press die mold. The methods of the present disclosure contemplate the actual fabrication of the deforming fixture, or the coordination of the manufacture by a third party entity or service provider. Exemplary custom deforming fixtures may be fabricated using a computer controlled rapid prototyping and tooling technique as known in the art. In other aspects, CNC type molds may also be used.

Once the custom deforming fixture if obtained, step 130 provides for the selection of a standard acetabular prosthesis blank from a set of pre-manufactured blanks, as will be described below. In various aspects, the set of pre-manufactured blanks may contain from between about 5 to about 15, or more, types of prostheses blanks, for example, each with a different sized cup or dome shape (including left and right variations). In various aspects, each acetabular prosthesis blank includes one or more flanges that are integrally formed with and radially extend from the cup portion. In other words, the acetabular prosthesis blank is preferably of a monolithic and single piece construction, including the cup portion and its flanges. Generally, the flanges are provided with a bone-facing surface that will be customized and deformed such that they are complementary to surfaces of the associated bones when the implant is affixed. With the use of a deforming fixture, as opposed to hand tools used by a surgeon, the flanges of the present disclosure may be provided with an increased thickness for additional strength, for example a thickness of from about 1 mm to about 5 mm, including about 1 mm to about 3 mm, or greater if so selected. It should also be understood that in certain aspects, however, it may be selected or otherwise necessary that the cup portion and flange(s) be separate elements that are joined together by known means. The flanges may also be fixedly adhered to the cup such as by welding.

Next, step 140 provides that the acetabular prosthesis blank is placed into the custom deforming fixture. It is envisioned that the custom deforming fixture is sized large enough to except the entire acetabular prosthesis blank therein. In certain aspects, however, for example where complex geometry may be required, the custom deforming fixture may be sized to accept a portion of the prosthesis, and in some aspects, only the flange(s) of the prosthesis. Once placed in the fixture, step 150 provides that a high press force is applied to bend or deform the flange(s), or otherwise alter the geometry, including the angular orientation, to achieve and match the desired patient-specific configuration. Although not required, it is also envisioned that the cup portion of the implant may also be customized using the deforming fixture, wherein certain areas of the cup portion may be shaped or deformed. Once removed from the fixture, as shown by step 160, the shaped acetabular prosthesis may then be thoroughly examined. In various aspects, follow-up measurements may be taken and compared to one or more of the original tomography data, geometry, or other measurement parameters previously obtained. Any necessary follow-up changes or modifications can be made such that the final shaped acetabular prosthesis will be able to substantially match the patient's pelvic anatomy relative to the patient's acetabulum without the need for further deformation during any surgical procedure.

Referring now to FIGS. 2-6, an exemplary acetabular prosthesis 10, according to one general embodiment, is shown to provide context of the methods of the disclosure. FIGS. 2A and 2B provide a standardized type of an acetabular prosthesis blank that may be used with the present disclosure. Additional specific descriptions of other exemplary acetabular prostheses can also be found in U.S. Pat. No. 7,713,306 and pending application Ser. No. 12/436,225 (published as U.S. Pub. No. 2010/0286789), commonly assigned to Biomet Manufacturing Corp., the entire specifications of which are incorporated herein by reference. The acetabular prosthesis 10 typically includes a modified hemispherical acetabular cup portion, or dome, 12. As described herein, the acetabular cup portion 12 is said to be "hemispherical" or "semi-hemispherical" in that it is not required to be a perfect hemisphere or portion thereof; but rather, it includes an arcuate portion, or rim, 14 extending along the periphery thereof without extending beyond the hemisphere of the acetabular cup 12. In various embodiments, however, the cup may have a rim that is positioned at least in part in a region greater than a hemisphere. In various aspects, each flange 32, 34, 36 of the standard blanks may be substantially planar, and a plurality of flanges may be substantially co-planar with one another as shown in FIG. 2B. Additionally, as shown in FIGS. 2B and 2C, the rim 14 of the blank 10 may define a plane, wherein the rim 14 (and its plane) is substantially parallel to the flanges 32, 34, 36 prior to shaping. In certain aspects, for example when there is a need for complex shape or geometry, one or more of portions of the flanges may optionally be pre-shaped as shown in FIG. 2C prior to using the custom deforming fixture. In this regard, the geometry of the pre-shaped blank may vary considerably, depending upon the final geometry that will be used to match the patient's bone structure.

The acetabular prosthesis 10 is preferably constructed from any suitable biocompatible material, such as titanium, including commercially pure (CP) titanium; stainless steel; titanium alloy; cobalt-chrome-molybdenum alloy; and the like.

It should be noted that the acetabular prosthesis 10 will normally also be associated with other components, such as a congruent shell or bearing liner (not shown) retained within the acetabular prosthesis 10 via bone cement or a ring lock (not shown), which are not depicted for purposes of clarity.

The acetabular cup 12 preferably includes a substantially concave inner surface 16 and a substantially convex outer surface 18, wherein the outer surface 18 is operable to be received in the acetabulum. The inner surface 16 may be either roughened or smooth, whereas the outer surface 18 may be smooth or roughened with a grit blast or a porous surface layer (not shown) to facilitate bone tissue in-growth. In various aspects, the outer surface 18 may be coated with a layer of porous plasma spray, or other known material that serves to increase or support bone ingrowth.

As shown, an area defining an optional receptacle or groove 20 is located in at least a portion of the outer surface 18 of the acetabular cup 12. The groove 20 may include tapered end portions 22, 24 if desired. The groove 20 is located in proximity to a peripheral surface of the acetabular cup 12, and generally in the superior and posterior region of the acetabular cup 12.

The acetabular cup 12 may include at least one, and generally, a plurality of throughbores 26 located therein, as shown in FIGS. 2-5. It should be noted that, as shown, the groove 20 may be bisected by at least one of the throughbores 26. The throughbores 26 provide a number of functions, such as enabling fastening members (not shown) to pass through the acetabular cup 12. Additionally, the throughbores 26 may provide for the infiltration of optional bone cement to improve adhesion, as well as providing for new bone tissue in-growth. At least one of the throughbores 28 typically includes a threaded surface 30 thereon for receiving an insertion instrument (not shown) for properly aligning the acetabular prosthesis 10 within the acetabulum. Throughbore 28 may also include a recessed area (not shown) that permits the insertion instrument to securely engage the acetabular cup 12 and permits controlled rotation of same. It will be noted that any graft material and/or bone cement should preferably be placed into the acetabulum before securing the acetabular cup 12 thereto.

As stated above, the acetabular prosthesis 10 includes at least one, and preferably two, or three or more substantially rigid, yet deformable, attachment or flange members 32, 34, 36 integrally formed with the acetabular cup 12 for fastening the acetabular prosthesis 10 to at least a portion of one or more surfaces of the pelvis (not shown), such as the ilium, pubis, and/or the ischium bone structures. By way of example, attachment member 32 may be used for attachment to the ischium, whereas attachment members 34 and 36 may be used for attachment to various surfaces of the ilium (e.g., anterior and posterior) or pubis. It is also envisioned that one or flange(s) may be removed from the blank if it is determined they are not necessary for the proper attachment of the prosthesis 10. The flanges may be removed with the die-press or in a separate operation.

In certain aspects, the shaping of the acetabular prosthesis blank using the custom deforming device may include the formation of one or more custom throughbore holes in the cup portion or one or more of the flanges. The throughbore(s) may be provided pre-drilled or punched in the acetabular blanks at standardized or common regions, or they may optionally be provided at customized locations to best meet the patient's custom geometry. Customized locations can be obtained by examining the patient-specific tomography data. For example, it may be desirable to place the throughbore(s) in locations known to have higher potential strength, and away from areas of the patient's bone that may be damaged or otherwise brittle or weak. With regard to providing custom throughbore(s), it is envisioned that they may be drilled or punched at any point during the process, for example, they may be formed within the blank prosthesis (prior to shaping) or they may be formed after the prosthesis is removed from the custom deforming fixture.

Figure 3A:
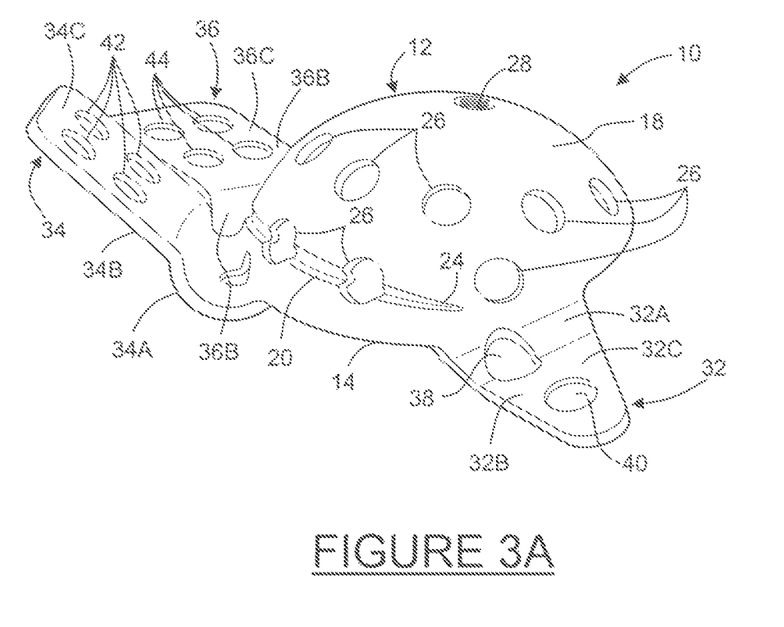
FIG. 3A is a rear perspective view of a custom shaped acetabular prosthesis, in accordance with various aspects of the present disclosure.
Figure 3B:
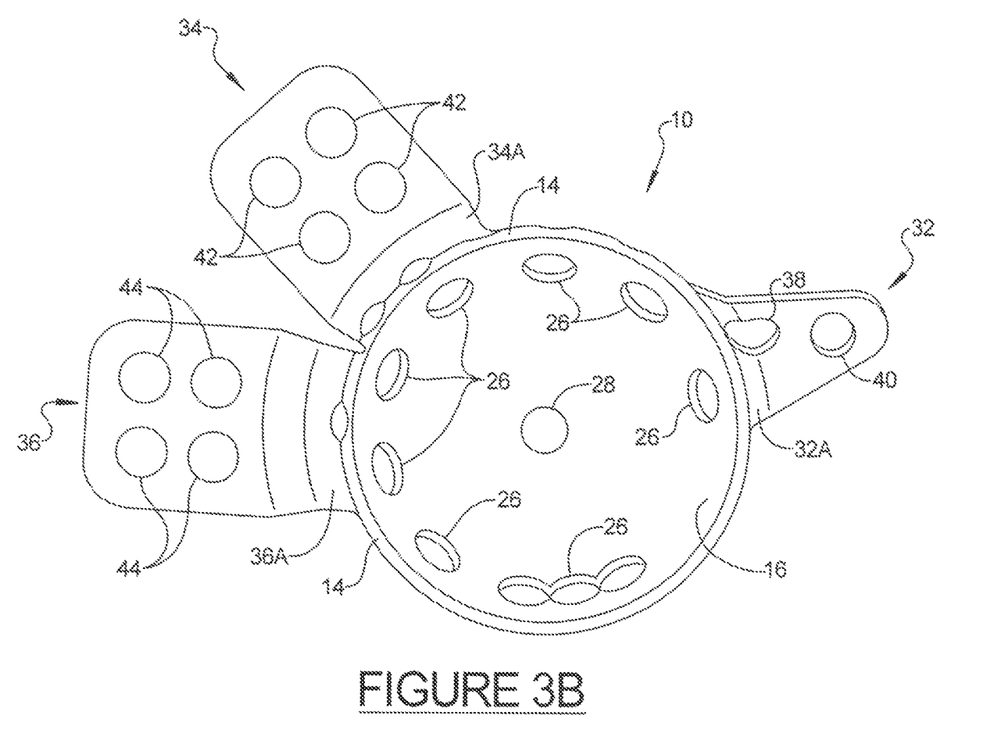
FIG. 3B is a front plan view of the custom shaped acetabular prosthesis as shown in FIG. 3A.
Figure 4:
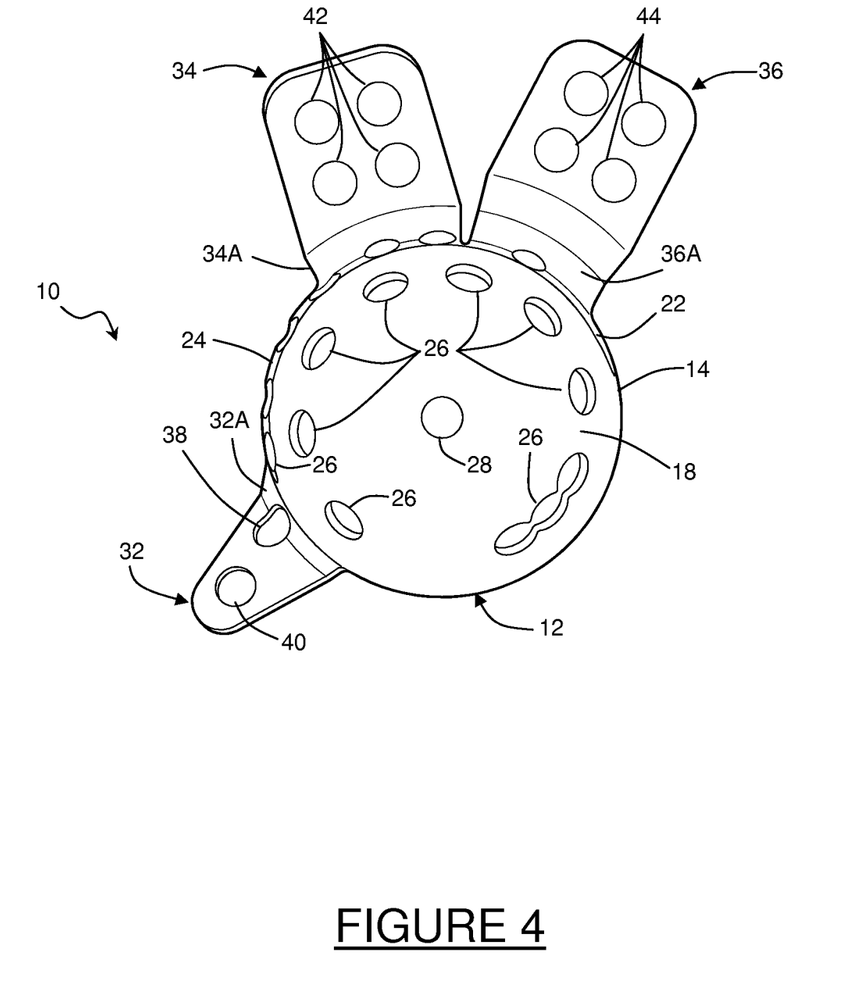
FIG. 4 is a rear plan view of the custom shaped acetabular prosthesis shown in FIG. 3A.

Attachment member 32 is shown as being substantially triangularly shaped; however, it is envisioned that the shape may be altered to other configurations. As shown in FIGS. 3-4, attachment member 32 may have two distinct portions, i.e., a first substantially curved portion 32A originating from, and contiguous with, the inner surface 16 of the acetabular cup 12, and a second substantially planar portion 32B extending out from, and angling away from, the first portion 32A. The curvature profile may be modified to meet any anatomical requirements based on the tomography data from the patient.

Attachment member 32 preferably includes at least one, and more preferably, a plurality of throughbores located therein. As shown in FIGS. 3-4, a throughbore 38 is provided in the curved portion 32A and another throughbore 40 is provided in the planar portion 32B. The throughbores 38, 40 provide a number of functions, such as enabling fastening members such as a surgical screw (not shown) to pass therethrough in order to allow the fastening member 32 to be secured to the ischium.

Attachment member 34 is shown as being substantially rectangularly shaped; however, it is envisioned that the shape may be altered to any other configuration known to those skilled in the art. As shown, attachment member 34 has two distinct portions, i.e., a first substantially curved portion 34A originating from, and contiguous with, the inner surface 16 of the acetabular cup 12, and a second substantially planar portion 34B extending out from, and angling away from, the first portion 34A. The curvature profile may be modified to meet any anatomical requirements based on the tomography data from the patient. Attachment member 34 may include at least one, and as shown, a plurality of throughbores 42 located therein. The throughbores 42 provide a number of functions, such as enabling fastening members such as a surgical screw (not shown) to pass therethrough in order to allow the fastening member 34 to be secured to at least a portion of a surface of the ilium.

Attachment member 36 is also shown as being substantially rectangularly shaped; however, it is envisioned that the shape may be altered to other configurations, including, for example, Y-shaped. As shown, attachment member 36 also has two distinct portions, i.e., a first substantially curved portion 36A originating from, and contiguous with, the inner surface 16 of the acetabular cup 12, and a second substantially planar portion 36B extending out from, and angling away from, the first portion 36A. Again, the curvature profile may be modified to meet any anatomical requirements, or based on the tomography data from the patient, as will be discussed below. Attachment member 36 preferably includes at least one, and more preferably, a plurality of throughbores 44 located therein to provide a number of functions, such as enabling fastening members such as a surgical screw (not shown) to pass therethrough in order to allow the fastening member 36 to be secured to at least another portion of a surface of the ilium spaced away from attachment member 34.

Figure 5:
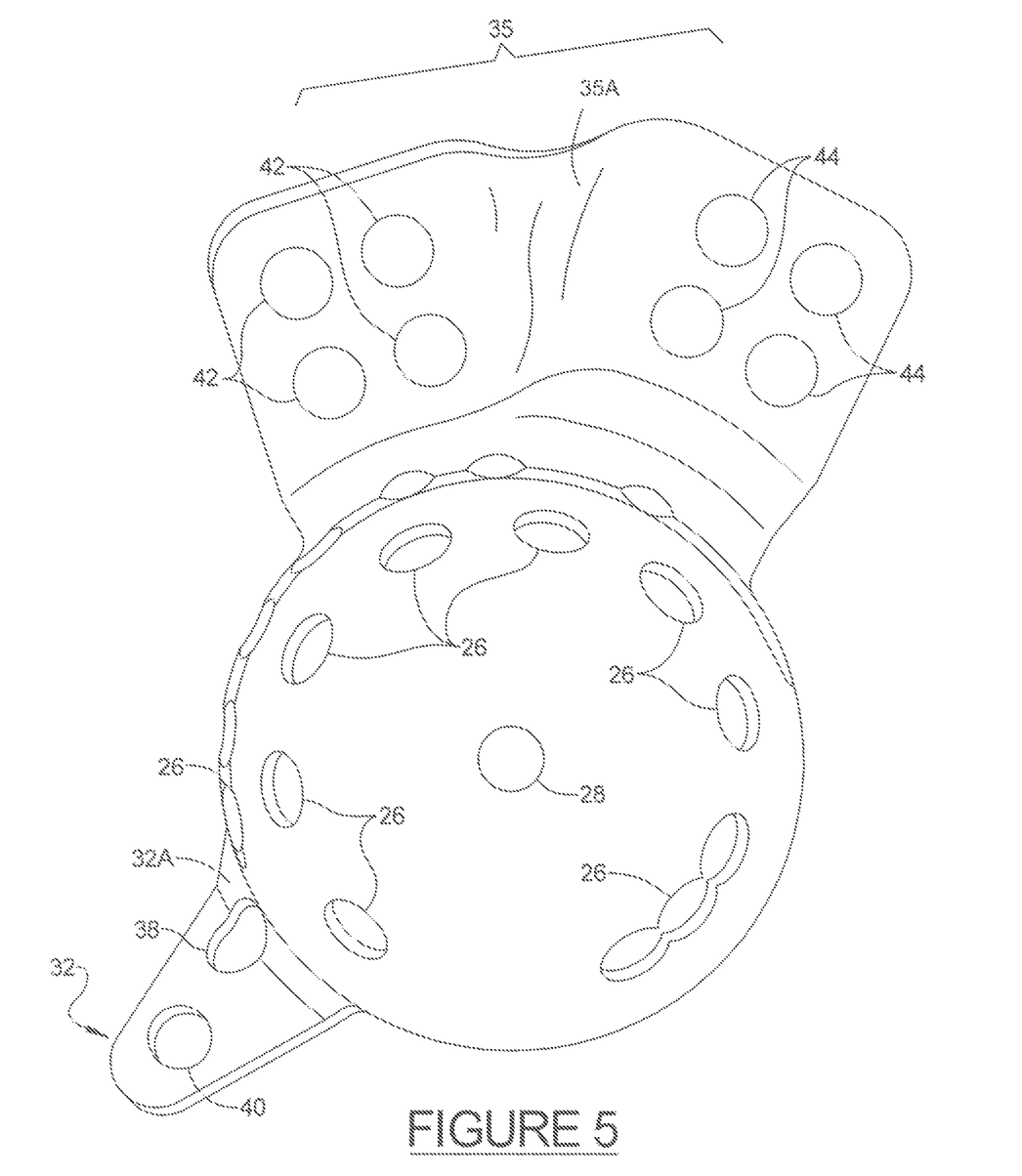
FIG. 5 is a rear plan view of another custom shaped acetabular prosthesis, in accordance with various aspects of the present disclosure.

FIG. 5 provides another aspect of the present disclosure that includes a larger type of flange 35. As shown, the middle portion 35A may be shaped having a curved contour or otherwise complex shaped geometry that may not otherwise be attained using the prior shaping techniques or hand tools. This is particularly true as the flange thickness is increased for additional strength. The use of a larger flange may provide additional stability. As with the other flanges 32, 34, 36, the larger flange 35 may be provided with various configurations and throughbores as desired.

The installation of the custom shaped acetabular prosthesis 10 can be accomplished in any number of ways, as are currently known in the art. The surgeon can typically surgically prepare the acetabulum and surrounding pelvic area to receive the acetabular prosthesis 10. This preparation would typically include removing any debris (e.g., bone fragments, bone cement) from the acetabulum. The surgeon would then install an allograft, if necessary, and install bone cement, if necessary, into the acetabulum. The acetabular cup 12 would then be received into, and anatomically aligned with, the acetabulum. At least one fastening member, such as a bone screw, would then be placed through one of the throughbores 26 and into the interior of acetabulum, thus securing the acetabular cup 12 to the acetabulum. The attachment members 32, 34, and 36 would then be secured to the ischium and ilium, respectively, with fastening members, such as surgical screws.

Figure 6:
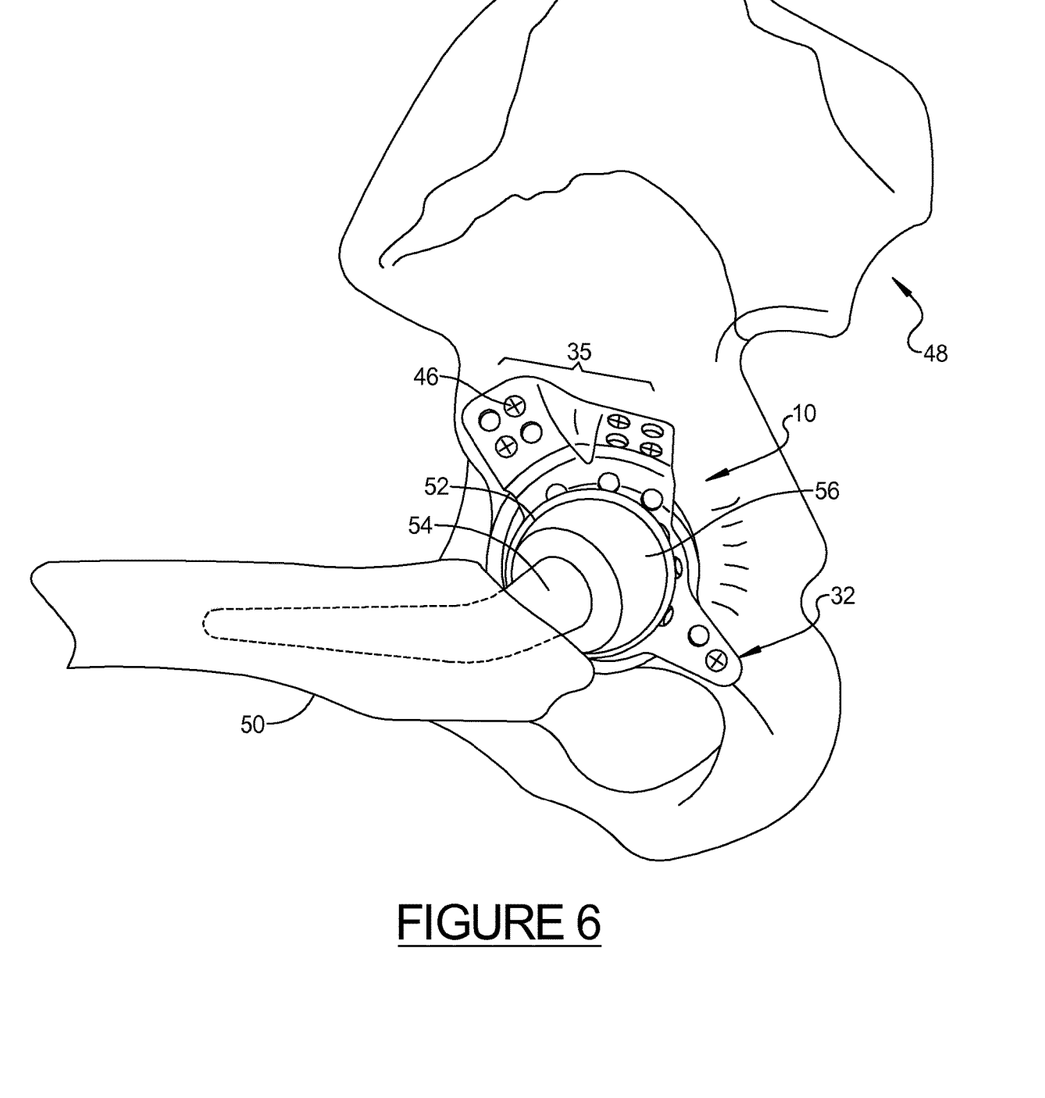
FIG. 6 illustrates a perspective view of a custom shaped acetabular prosthesis implanted in an acetabulum.

FIG. 6 generally illustrates an exemplary acetabular prosthesis made in accordance with the present disclosure implanted in an acetabulum of the pelvis area 48. As described above, one or more custom shaped connecting flanges 32, 35 can be configured to engage the remaining healthy portions of the hip bone. Bone screws 46, or other fastening means can be driven though the custom shaped connecting flanges and into the hip bone to secure the acetabular prosthesis. It will be appreciated that the custom shaped connecting flanges can be connected to various locations within or near the pelvis anatomy, and may particularly include non-limiting areas such as the ilium, pubis, and ischium bone structures as previously described. Of course, as determined by the surgeon or others skilled in the art, the connecting flanges 32, 35 can also be located at other locations of the hip region to facilitate connection to other portions of the pelvis with bone screws 46 or other suitable fasteners such as bone cement or a porous material to promote bone growth into the connecting flanges. The cup portion of the prosthesis 10 may be fitted with a liner 52 that accepts the head 56 of the femur 50, connected by a stem or neck portion 54.

The embodiments described herein are exemplary and not intended to be limiting in describing the full scope of compositions and methods of the present technology. Equivalent changes, modifications and variations of embodiments, materials, compositions and methods can be made within the scope of the present technology, with substantially similar results.

What is claimed is:

1. A method of making a custom acetabular implant for a patient, the method comprising:
    analyzing tomography data of the patient and obtaining geometry and measurement parameters of the patient's pelvic anatomy for formation of a custom deforming fixture;
    selecting an acetabular prosthesis blank from a plurality of pre-manufactured acetabular prosthesis blanks, each acetabular prosthesis blank including a cup portion and at least one flange formed integrally with the cup portion and extending radially outward from a rim of the cup portion, the at least one flange configured for attachment to the patient's pelvic anatomy; and
    deforming the at least one flange using the custom deforming fixture to form a custom acetabular prosthesis, wherein the custom acetabular prosthesis has a final shaped geometry and measurement parameters that match the patient's pelvic anatomy relative to the patient's acetabulum,
    wherein deforming the acetabular prosthesis blank comprises placing the acetabular prosthesis blank into the custom deforming fixture and applying a press force to the custom deforming fixture, thereby bending or altering the flange's angular orientation to match a patient specific configuration based on the analyzed tomography data.

2. The method according to claim 1, wherein analyzing the tomography data comprises using computer aided design software to create a three dimensional representation of the patient's pelvic anatomy.

3. The method according to claim 1, wherein obtaining geometry and measurement parameters includes obtaining data relative to at least one of the ischium, pubic, and ilium bone structures of the patient.

4. The method according to claim 1, wherein the tomography data comprises image data obtained from scanning techniques selected from the group consisting of computed tomography (CT), magnetic resonance imaging (MRI), positron emission tomography (PET), and combinations thereof.

5. The method according to claim 1, wherein the custom deforming fixture comprises a two-piece press die mold.

6. The method according to claim 5, wherein the two-piece press die mold is formed to have a geometry and measurement parameters that match the patient's pelvic anatomy relative to the patient's acetabulum.

7. The method according to claim 1, further comprising fabricating or coordinating the manufacture of the custom deforming fixture based on at least one of the tomography data, the geometry, and the measurement parameters of the patient's pelvic anatomy.

8. The method according to claim 7, wherein the custom deforming fixture is fabricated using a computer controlled rapid prototyping and tooling technique.

9. The method according to claim 1, wherein the acetabular prosthesis blank comprises a plurality of flanges integrally formed with and radially extending from the cup portion.

10. The method according to claim 1, further comprising pre-shaping at least a portion of the flange of the acetabular prosthesis blank prior to using the custom deforming fixture.

11. The method according to claim 1, further comprising providing the flange of the acetabular prosthesis blank planar.

12. The method according to claim 11, wherein the rim defines a rim plane, and the rim plane is parallel to the flange prior to deforming.

13. A method of making a custom acetabular implant for a patient, the method comprising:
    analyzing acquired tomography data of the patient and obtaining geometry and measurement parameters of the patient's pelvic anatomy;
    obtaining a custom deforming fixture having dimensions modeled after the tomography data and matching the geometry and measurement parameters relative to the patient's acetabulum;
    selecting an acetabular prosthesis blank from a plurality of pre-manufactured acetabular prosthesis blanks that include a cup portion with at least one integral flange radially extending outward therefrom, the selected blank having measurement parameters matching the patient's pelvic anatomy; and
    customizing and shaping the acetabular prosthesis blank using the deforming fixture to shape the flange so as to create a shaped acetabular prosthesis, such that the shaped acetabular prosthesis will mate with the patient's pelvic anatomy relative to the patient's acetabulum,
    wherein customizing and shaping the acetabular prosthesis blank comprises bending the integral flange or altering the integral flange's angular orientation relative to the cup portion to match a patient-specific configuration.

14. The method according to claim 13, wherein obtaining the custom deforming fixture comprises obtaining a two-piece press die mold.

15. A method of making a custom acetabular implant for a patient, the method comprising:
    analyzing tomography data and obtaining geometry and measurement parameters of the patient's pelvic anatomy;
    determining a patient-specific configuration of the patient's pelvic anatomy relative to the patient's acetabulum;
    obtaining a custom press die mold having dimensions matching the patient-specific configuration;
    selecting an acetabular prosthesis blank from a plurality of pre-manufactured monolithic acetabular prosthesis blanks including a cup portion and a plurality of integrally formed flanges radially extending outward therefrom, the selected blank having measurement parameters matching the patient's pelvic anatomy; and
    deforming the acetabular prosthesis blank using the custom press die mold and shaping at least one of the plurality of flanges to achieve the patient-specific configuration,
    wherein shaping at least one of the plurality of flanges comprises placing the acetabular prosthesis blank into the custom press die mold and applying a press force to the mold, thereby bending the flange or altering its angular orientation to match the patient-specific configuration.

16. The method according to claim 15, further comprising fabricating a custom press die mold using a computer controlled rapid prototyping and tooling technique.

17. The method according to claim 15, wherein the plurality of integrally formed flanges of the acetabular prosthesis blank are co-planar prior to shaping.

* * * * *